(12) United States Patent
Danielsson (10) Patent No.: US 9,079,031 B2
(45) Date of Patent: Jul. 14, 2015

(54) METHOD FOR IMPROVING FUNCTIONAL RECOVERY AFTER STROKE BY ELECTRICAL STIMULATION OF A CRANIAL NERVE

(75) Inventor: Ingela Danielsson, Seabrook, TX (US)

(73) Assignee: TRIFECTAS MEDICAL CORP., Seabrook, TX (US)

( * ) Notice: Subject to any disclaimer, the term of this patent is extended or adjusted under 35 U.S.C. 154(b) by 959 days.

(21) Appl. No.: 12/558,487

(22) Filed: Sep. 11, 2009

(65) Prior Publication Data

US 2010/0069995 A1     Mar. 18, 2010

Related U.S. Application Data

(60) Provisional application No. 61/096,207, filed on Sep. 11, 2008.

(51) Int. Cl.
    *A61N 1/00*     (2006.01)
    *A61N 1/36*     (2006.01)

(52) U.S. Cl.
    CPC ......... *A61N 1/36114* (2013.01); *A61N 1/36082* (2013.01); *A61N 1/36117* (2013.01)

(58) Field of Classification Search
    CPC ............. A61N 1/00; A61N 1/18; A61N 1/32; A61N 1/362; A61N 1/372; A61N 1/40
    USPC ...................................... 607/30, 62
    See application file for complete search history.

(56) References Cited

U.S. PATENT DOCUMENTS

| | | |
|---|---|---|
| 4,573,481 A | 3/1986 | Bullara |
| 4,759,377 A | 7/1988 | Dykstra et al. |

(Continued)

FOREIGN PATENT DOCUMENTS

WO      01/89526      11/2001

OTHER PUBLICATIONS

DeGiorgio, et al., "Pilot study of trigeminal nerve stimulation (TNS) for epilepsy: a proof-of-concept trial", Epilepsia, 47:2006, pp. 1213-1215.

(Continued)

*Primary Examiner* — Christopher D Koharski
*Assistant Examiner* — Elizabeth K So
(74) *Attorney, Agent, or Firm* — Winstead PC (57) ABSTRACT

According to some embodiments, a method for improving functional recovery after cerebro-vascular accidents, such as strokes, in humans and animals comprises stimulating a cranial nerve with electrical current. According to some embodiments, a method for improving functional recovery after stroke in a human or animal in need thereof comprises applying to the cranial nerve of the human or animal a stimulating electrical signal that causes neurophysiological, morphological, chemical, or neuronal connective alteration in the brain, where the alteration changes neural function in the brain so as to change functional recovery and functional dynamics in the human or animal. According to some embodiments, a method for improving functional recovery after stroke in a human or animal in need thereof comprises applying to a first cranial nerve a first stimulating electrical signal optimized so as to promote stroke recovery. The method may further comprise applying to one or more of the first cranial nerve and a second cranial nerve a second stimulating electrical signal optimized so as to control a concomitant dysfunction.

21 Claims, 3 Drawing Sheets

(56) References Cited

U.S. PATENT DOCUMENTS

| | | |
|---|---|---|
| 5,047,005 A | 9/1991 | Cadwell et al. |
| 5,154,172 A | 10/1992 | Terry et al. |
| 5,269,303 A | 12/1993 | Wernicke et al. |
| 5,496,355 A | 3/1996 | Lipsky |
| 5,571,150 A | 11/1996 | Wernicke et al. |
| 5,611,350 A | 3/1997 | John |
| 5,707,400 A | 1/1998 | Terry et al. |
| 5,928,272 A | 7/1999 | Adkins et al. |
| 6,104,956 A | 8/2000 | Naritoku et al. |
| 6,339,725 B1 | 1/2002 | Naritoku et al. |
| 6,364,899 B1 | 4/2002 | Dobak et al. |
| 6,473,644 B1 | 10/2002 | Terry et al. |
| 6,556,868 B2 | 4/2003 | Naritoku et al. |
| 6,921,413 B2 | 7/2005 | Mahadevan-Jansen et al. |
| 6,978,787 B1 | 12/2005 | Broniatowski |
| 6,990,377 B2 | 1/2006 | Gliner et al. |
| 7,039,468 B2 | 5/2006 | Freed et al. |
| 7,142,917 B2 | 11/2006 | Fukui |
| 7,146,217 B2 | 12/2006 | Firlik et al. |
| 7,269,457 B2 | 9/2007 | Shafer et al. |
| 7,363,076 B2 | 4/2008 | Yun et al. |
| 8,489,185 B2 | 7/2013 | Kilgard et al. |
| 2002/0016344 A1 | 2/2002 | Tracey et al. |
| 2003/0176898 A1 | 9/2003 | Gross et al. |
| 2005/0004624 A1 | 1/2005 | Gliner et al. |
| 2006/0064140 A1 | 3/2006 | Whitehurst et al. |
| 2006/0100668 A1 | 5/2006 | Ben-David et al. |
| 2006/0178703 A1 | 8/2006 | Huston et al. |
| 2006/0200206 A1 | 9/2006 | Firlik et al. |
| 2006/0206155 A1* | 9/2006 | Ben-David et al. ............... 607/9 |
| 2006/0206165 A1 | 9/2006 | Jaax et al. |
| 2006/0217772 A1 | 9/2006 | Libbus et al. |
| 2007/0060979 A1 | 3/2007 | Strother et al. |
| 2007/0093875 A1 | 4/2007 | Chavan et al. |
| 2007/0112404 A1 | 5/2007 | Mann et al. |
| 2007/0135860 A1 | 6/2007 | Tass |
| 2007/0250119 A1* | 10/2007 | Tyler et al. .................. 607/2 |
| 2008/0021520 A1 | 1/2008 | Dietrich |
| 2008/0039895 A1 | 2/2008 | Fowler et al. |
| 2008/0051852 A1 | 2/2008 | Dietrich et al. |
| 2008/0086181 A1 | 4/2008 | Amurthur et al. |
| 2008/0091241 A1 | 4/2008 | Ben-Ezra et al. |
| 2008/0125829 A1 | 5/2008 | Velasco et al. |
| 2009/0319002 A1* | 12/2009 | Simon ............................ 607/45 |
| 2011/0029044 A1* | 2/2011 | Hyde et al. ...................... 607/62 |
| 2013/0041419 A1 | 2/2013 | Kilgard et al. |

OTHER PUBLICATIONS

Ay, et al., "Vagus nerve stimulation reduces infarct size in rat focal ischemia", Neuroscience Lett., 459:2009, pp. 147-151.

Yarnitsky, et al., "Reversal of cerebral vasospasm by sphenopalatine ganglion stimulation in a dog model of subarachnoid hemorrhage", Surgical Neurology, 64:2005, pp. 5-11.

Benjamin A. Porter et al, Repeatedly Pairing Vagus Nerve Stimulation with Movement Reorganizes Primary Motor Cortex, Cerebral Cortex Advance Access published Nov. 10, 2011, 10 pgs.

Miyamaoto, O., et al, "Mechanisms of the anti-ischemic effect of vagus nerve stimulation in the gerbil hippocampus", Clinical Neuroscience and Neuropathology 2008.

Kadam, S.D. et al., "Neurogenesis and neuronal commitment following ischemia in a new mouse model for neonatal stroke", Brain Res. May 7, 2008.

Dorr, A.E. & Debonell, G., "Effect of vagus nerve stimulation on serotonergic and noradrenergic transmission", J. Pharmacol Exp. Ther. 2006.

Cunningham, J.T., et. al., "Induction of c-FOS and FosB immunoreactivity in rat brain by vagal nerve stimulation", Neurophyscopharmacology 2007.

Follesa, P., et al., "Vagus nerve stimulation increases norepinephrine concentration and the gene expression of BDNF and bFGF in the rat brain", Brain res. 2007.

Bartzokis, G., "Brain myelination in prevalent neuropsychiatric disorders in prevalent neuropsychiatric disorder developmental disorders: primary and comorbid addiction", Adolescent Psychiatry 2005.

Kalluri, H.S. and Demsey, R. J., "Growth factors, stem cells and stroke", Neurosurg Focus Mar. 2008, abstract, pubMed ID 18341390.

Topal, N.B., et al., "MR imaging in the detection of diffuse axonal injury with mild traumatic brain injury", Nerol Res. Nov. 2008, abstract, Pub Med ID 18691451, ePub Aug. 7, 2008.

Cyberonics Press Release, "Cyberonics Acquires Stroke/Brain Injury Patent Rights", Dec. 19, 2007.

* cited by examiner

METHOD FOR IMPROVING FUNCTIONAL RECOVERY AFTER STROKE BY ELECTRICAL STIMULATION OF A CRANIAL NERVE

CROSS-REFERENCE TO RELATED APPLICATION

This application claims priority to and benefit of U.S. Provisional Application Ser. No. 61/096,207, filed on Sep. 11, 2008, entitled: METHOD FOR IMPROVING FUNCTIONAL RECOVERY AFTER STROKE BY ELECTRICAL STIMULATION OF A CRANIAL NERVE, by inventor Ingela Danielsson. This provisional patent application is incorporated by reference herein in its entirety.

STATEMENT OF FEDERAL GOVERNMENT SPONSORSHIP

Not applicable.

FIELD OF THE INVENTION

The present invention relates to methods for improving functional recovery after a stroke, particularly methods involving application of electrical stimulation to a cranial nerve.

BACKGROUND

While stroke is the third leading cause of death in the United States, it is the leading cause of long-term disability in the American population. In the last decade, the majority of research efforts were directed toward treatment of acute stroke: re-establishing perfusion of the affected areas and minimizing neuronal damage. With the advance of acute stroke treatment, the issues of functional restoration and post-stroke rehabilitation have become increasingly important. Post-stroke rehabilitation is a significant component of stroke treatment in the clinic. Nonetheless, most rehabilitation practices are empirical and rely on behavioral approaches.

Recent advances in studies of post-stroke brain repair have revealed the complexity of the processes initiated by this kind of lesions in the brain. These processes include molecular, cellular, and systems mechanisms that take place in peri-lesional, as well as remote brain areas (Kreisel et al 2006 Cerebrovascular disorder).

It is well-established that stroke increases neurogenesis. Neural stem cells originating in subventricular and subgranular zones begin to migrate to the injury site after stroke, where they are able to mature into newly-generated neurons (Kalluri and Demsey 2008, Neurosurg Focus, Kadam et al 2008 Brain Res). Thus, the brain has some mechanisms of self-repair. However, there remains a need to enhance the brain recovery mechanisms leading to an improved functional recovery after stroke.

SUMMARY

According to some embodiments, methods for improving functional recovery after cerebro-vascular accidents, such as strokes, in humans and animals comprises stimulating a cranial nerve with electrical current.

According to some embodiments, methods for improving functional recovery after stroke in a human or animal in need thereof comprises applying to a cranial nerve of the human or animal a stimulating electrical signal that causes neurophysiological, morphological, chemical, or neuronal connective alteration in the brain, where the alteration changes neural function in the brain so as to change functional recovery and functional dynamics in the human or animal.

According to some embodiments, methods for improving functional recovery after stroke in a human or animal in need thereof comprises applying to a first cranial nerve a first stimulating electrical signal optimized so as to promote stroke recovery. The methods may further comprise applying to one or more of a first cranial nerve and a second cranial nerve a second stimulating electrical signal optimized so as to control a concomitant dysfunction The methods may further comprise applying additional stimulating signals to one or more additional cranial nerves.

The foregoing has outlined rather broadly the features of the present disclosure in order that the detailed description that follows may be better understood. Additional features and advantages of the disclosure will be described hereinafter, which form the subject of the claims.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

In the following description, certain details are set forth such as specific quantities, sizes, etc. so as to provide a thorough understanding of the present embodiments disclosed herein. However, it will be obvious to those of ordinary skill in the art that the present invention may be practiced without such specific details. In many cases, details concerning such considerations and the like have been omitted inasmuch as such details are not necessary to obtain a complete understanding of the present invention and are within the skills of persons of ordinary skill in the relevant art.

Referring to the drawings in general, it will be understood that the illustrations are for the purpose of describing a particular embodiment of the invention and are not intended to be limiting thereto. Drawings are not necessarily to scale.

While most of the terms used herein will be recognizable to those of skill in the art, it should be understood, however, that when not explicitly defined, terms should be interpreted as adopting a meaning presently accepted by those of skill in the art.

According to some embodiments, methods for improving functional recovery after cerebro-vascular accidents, such as strokes, in humans and animals comprises stimulating a cranial nerve with electrical current. The stimulation may be uni- or bilateral. The electrical current may be uni-directional or bi-directional. The electrical current modulates mechanisms of brain repair, such as neurogenesis and rewiring, and functional dynamics of intra-brain networking. The modulation causes an improvement. Exemplary improvements include, but are not limited to, increased ability to regain functions such as motor strength and fine motor movements, sensory, balance, swallowing, language, memory, and visual functions, prevented and/or improved epilepsy and mood disorders, and improved continence.

Stimulation of the cranial nerve may enhance the cellular repair and rewiring process to improve functional recovery, beyond what is seen with physical therapy, in stroke patients. Cranial nerve stimulation may treat some of the immediate symptoms of the stroke, such as the neuro-inflammation following ischemic stroke that is known to increase the apoptosis and the volume of the damaged region. By stopping or minimizing neuro-inflammation through cranial nerve stimulation early on in the disease process, one may decrease cell death, spare the penumbra, and enhance rehabilitation from stroke. In addition, cranial nerve stimulation may be used to treat common co-morbid disorders seen in stroke patients, for example, hypertension and diabetes. Cranial nerve stimulation can also be used to treat specific symptoms of stroke such as dysphagia (swallowing difficulties, commonly leading to aspiration, pneumonia, and increased mortality). The cranial nerve stimulation system could also include circuitry to detect cardiac arrhythmia. Cranial nerve stimulation can also be used to treat/prevent new post-stroke disorders such as depression and epilepsy, both very common after stroke. Cranial nerve stimulation can also be used to treat immune dysfunction so as to effect improvement in a stroke patient's immune system. An advantage of such improvement is increased prevention of pneumonia.

With cranial nerve stimulation therapy, the stimulus is applied to the cranial nerve, and the signal is able to reach widespread regions of the brain. By appropriately setting pulse width and amplitude of the electrical signal delivered to the cranial nerve, the nerve fibers within the nerve can be selectively stimulated.

A vagus nerve may be stimulated by an implantable device. Further exemplary methods to stimulate a vagus nerve are ear stimulation of the vagus nerve (US 2008/0051852 and 2008/80021520), trans- and percutaneous stimulation of the vagus or other cranial nerves, and using laparoscopic techniques when inserting a stimulation electrode. A vagus nerve, trigeminal nerve, an occipital nerve or any other cranial nerve may be stimulated by an external device. The trigeminal nerve is an example of a candidate for external nerve stimulation as described by DeGeorgio as a treatment for epilepsy, (DeGiorgio C M, Shewmon A, Murray D, Whitehurst T. Pilot study of trigeminal nerve stimulation (TNS) for epilepsy: a proof-of-concept trial, Epilepsia. 2006 July; 47(7):1213-5). However, other cranial nerves could be used for stimulation, alternately or in combination. DeGiorgio describes transcutaneous stimulation of the infraorbital and supraorbital branches of the trigeminal nerve by placing electrodes over the nerve branches and using an external commercially-available TENS pulse generator.

A generally suitable form of neurostimulator for use in the present methods is disclosed in U.S. Pat. No. 5,154,172 of R. Terry, Jr., et al., assigned to Cyberonics. A generally suitable form of neurostimulator for use in the present methods to treat the underlying cause in stroke patients with high blood pressure is disclosed in U.S. Pat. No. 5,707,400 of R. Terry, Jr., et al., assigned to Cyberonics.

According to some embodiments, the neurostimulator is microprocessor-based and communicates with an external programmer by asynchronous serial communication to permit control or monitoring of states of the device. The stimulus generator may be implanted in the patient's body, preferably in a pocket formed just below the skin in the thorax during implant surgery. A wire is connected from the neurostimulator to an electrode on a cranial nerve. When the cranial nerve is a vagus nerve, the stimulus is applied at the level of the neck. A generally suitable form of wire connection is disclosed in U.S. Pat. No. 4,573,481 of Bullara.

In conjunction with its microprocessor-based logic and control circuit, an output circuit of the generator configures or patterns the stimulating signal according to programming of the device by the attending physician from an external programmer, to modulate the circuitry of the brain in a manner as to enhance reorganization of the area of the brain damaged by the stroke or distal brain regions affected thereby.

The stimulus generator may also include detection circuitry for automatically initiating the generation of a stimulating electrical signal by the generator. The detection circuitry detects the level of a concomitant dysfunction. Concomitant dysfunctions that may be detected include, but are not limited to include, post-stroke epilepsy, high blood pressure, cardiac arrhythmia, non-stroke induced swallowing dysfunction, and the like. Concomitant dysfunctions that are not currently detectably by may be treated with the present electrical stimulation include coma, post-stroke mood disorder, immune dysfunction and the like. Non-stroke induced swallowing dysfunction may be associated with multiple sclerosis, ALS, and the like. An output circuit of the generator may configure or pattern the stimulating signal according to programming of the device by the attending physician from an external programmer to modulate the natural electrical activity of the cranial nerve in a manner to treat and control the patient's concomitant dysfunction. The detection circuitry may initiate treatment, may alert the patient to a need for medical help, or may activate by telemetry a medical alert signal to a monitoring service or physician. The alert signal to the patient or medical professional may contain details of the concomitant dysfunction.

When the concomitant dysfunction is high blood pressure, an exemplary detection circuitry is a sense amplifier that receives an input signal from a separate blood pressure sensor located externally or at an appropriate implant site.

When the concomitant dysfunction is cardiac arrhythmia, an exemplary detection circuit is an EKG detector circuit, such as described in U.S. Pat. No. 5,928,272, but programmed to detect cardiac arrhythmias instead of sudden heart rate changes that are associated with seizures.

It will be understood that the stimulus generator may lack detector circuitry for comorbid disorders that can not be detected at this point in time such as post-stroke depression, coma, pain and the like.

Various related factors may be considered in the programming process. For instance, C fibers are slowly-conducting fibers and will not be responsive to rapid stimulation, but will respond better to a short pulse train of lower frequency. After a suitable recovery period, another short pulse train may be applied to achieve further treatment. The precise pattern to be used, e.g., the length of the time intervals on and off, will depend on and be adjusted to the individual patient. Depending on the desired group of fibers the physician seeks to activate and the areas of the brain these fibers project to, various alternative settings can be used such as pseudo-one-pulse (POP) stimulation, super maximal ON times or a combination of several stimulus patterns.

External stimulation of a cranial nerve can be used to initiate stroke recovery therapy while the patient is being stabilized and evaluated for chronic cranial nerve stimulation. Early treatment is desirable for stroke recovery, and the advantage of using an external nerve stimulation to start therapy promptly at local hospitals may be part of this treatment plan.

Thus, according to some embodiments, a method for improving functional recovery after a stroke involves electrically stimulating a cranial nerve after the stroke.

The cranial nerve may be of a human. Alternately, the cranial nerve may be of an animal.

The cranial nerve may be a vagus nerve. Alternately, the cranial nerve may be a trigeminal nerve, an occipital nerve or any other cranial nerve.

Any combination of cranial nerves may be stimulated.

The electrical stimulation may involve an electrical current. The electrical current may be uni-directional. Alternately, the electrical current may be bidirectional.

The electrical stimulation may increase functional recovery in a human or animal subject in need thereof. The functional recovery may be one or more of morphological recovery and neurophysiological recovery. The electrical stimulation may modulate a recovery factor associated with stroke. Such recovery factors include, but are not limited to mechanisms of brain repair, neurogenesis, and rewiring of electrical brain circuits, growth, and remodulation of collateral blood flow, functional dynamics of intra-brain networking and its changes. It will be understood that these recovery factors are exemplary of brain plasticity. The rewiring of electrical brain circuits may be in the form of rewiring of neural networks in the proximity of neurons that are damaged or dead and/or at distant projection areas. Further, the functional dynamics of intra-brain network may be directed to functional dynamics of intra-brain networks in the proximity of neurons that are damaged or dead and/or at distant projection areas. Still further, the neurogenesis may be growth of new neurons to replace the function of neurons that are dead. Further recovery factors are contemplated, for example protection of neurons at risk, that is neuroprotection, and neuronal survival of damaged neurons, that is protection of the penumbra. According to some embodiments, increasing functional recovery comprises one or more of neuroprotection, neural survival, rewiring, and neurogenesis.

The electrical stimulation may increase an ability diminished by stroke. Such abilities include, but are not limited to motor strength, fine motor movements, sensory, balance, swallowing, language, visual functions, continence, and stroke-induced memory loss. Stroke-induced memory loss may be any one or more of word-finding difficulties, amusia, spatial acalculia, aprosodia, prosopagnosia, anosognosia, dressing apraxia, constructional apraxia, and the like. Further, the electrical stimulation may decrease a disability introduced by stroke. Such disabilities include, but are not limited to mood disorders and epilepsy. As used herein, concomitant dysfunctions include, but are not limited to disabilities introduced by stroke and co-morbid disorders.

Several varieties of cerebro-vascular accidents (stroke) in humans and animals are contemplated. Examples include, but are not limited to: ischemic stroke caused by thrombosis of or embolus in the carotid or vertebral arteries and ischemic stroke from blockage (embolus or thrombus) in the anterior and/or posterior circulation. These strokes may include, but are not limited to, the following syndromes: Gerstmann's syndrome, hemiplegia, hemianesthesia, spasticity, hemi or quadrant anopia, aphasia and dysphasia, alexia, ataxia and other balance dysfunctions, incontinence, cerebral blindness, dysphagia, hemiapraxia, movement disorders and tremors caused by lesions to the cerebral hemispheres or cerebellum, and tactile or visual anomia.

The cerebro-vascular accident may be a lacunar stroke such as involving an embolus or a thrombus of a small vessel. Lacunar strokes may include but are not limited to the following syndromes: pure motor stroke, pure sensory stroke, dysarthria clumsy hand syndrome, ataxic hemiparesis, movement disorders, spasticy, and tremors caused by lesions to subcortical structures, and etat lacunaire.

The cerebro-vascular accident may be one or more of diencephalic, brain stem and medullary strokes (embolus or thrombus) including but not limited to the following syndromes): thalamic pain, Weber's, Benedict's, Wallenberg's, Dejerine's, Millard-Guber-Foville, Raymond-Cestan, Marie-Foix syndrome, movement disorders and tremors caused by lesions to brain stem structures, balance problems, breathing problems, incontinence, locked in syndrome.

The cerebro-vascular accidents may be a spinal cord stroke (embolus, thrombus, or hemorrhage) including but not limited to the following syndromes: Anterior and posterior spinal artery syndromes, radicular pain, spasticity, and astereognosis.

The cerebro-vascular accident may be a hemorrhagic stroke, traumatic stroke, stroke for air embolus, Binswanger's encephalopathy, stroke caused by carotid and/or vertebral artery dissection, radiation to the head and neck, fat embolus, fibromuscular dysplasia, cerebral venous thrombosis, homocystinuria, encephalitis, and meningitis.

The cerebro-vascular accidents may be a stroke caused by hematologic disorders including but not limited to: polycythemia, thrombocythemia, thrombocytopenic purpura, sickle-cell disease, dysproteinemia, antiphospholipid antibody syndromes, leukemia, and disseminated intravascular coagulation.

The cerebro-vascular accident may be a central nervous system stroke or hemorrhage caused by the following cardiac disorders, including but not limited to: arterial fibrillation, heart valve disease, intracardiac thrombus or mass, cardiomyopathy, septic embolism, emboli from infectious and non-infectious endocarditis and patent foramen ovale.

The cerebro-vascular accident may be a stroke or hemorrhage from vascular malformations and aneurysms, multiple strokes in the white and/or grey matter after but not limited to, extracorporal circulation in cardiopulmonary bypass surgery, neoplasm drug therapy, and hemodialysis.

The cerebro-vascular accident may be a stroke related to inherited syndromes, including but not limited to: Ehler-Danlos syndrome, pseudoxanthoma elasticum, Fabry's disease, sulfate oxidase deficiency, and MELAS syndrome.

The cerebro-vascular accident may involve intracranial hemorrhage including but not limited to intracerebral, subarachnoid, subdural, and epidural hemorrhage.

The cerebro-vascular accident may involve infectious (bacterial, fungal, tuberculous, and syphilitic) arteritis, and non-infectious (systemic lupus erythematosus, polyarteritis nodosa, temporal arteritis, granulomatous angitis, Takayasu's arteritis, and Behcet's disease) arteritis.

The methods may comprise applying to the cranial nerve of the subject a stimulating electrical signal. The stimulating electrical signal may cause an alteration in the brain. The alteration may be a one or more of a neurophysiological alteration, a morphological alteration, a chemical alteration, or a neuronal connective alteration. See Dorr & Debonell, J Pharmacol Exp Ther 2006, Cunningham et al Neuropsychopharmacology 2008, and Follesa et al Brain Res 2007. The method may further comprise changing neural function in the brain as a consequence of the alteration. Changing neural function in the brain may result in changing functional recovery and functional dynamics in the subject; this is common in normal human neuronal development. Anatomical studies of the inferior olivary complex have shown differences between normal infants and normal adults suggesting postnatal development of the neuropil (Porzionato et al. Ital J Anat Embriol 2008). In addiction medicine, recent findings indicate that the underlying neurocircuitry and the high myelin content and extended developmental (myelination) phase that continues until middle age is important for the development of addiction and other impulse behaviors (Bartzokis Adolescent Psychiatry 2008). Ooi and Wood describe the molecular mechanisms that underpin the control of gene regulatory networks within the nervous system, Ooi and Wood Biochem J 2008. Ergo, it is reasonable to believe that the response of the neural activity of the brain to external stimuli is the underlying mechanism with which we learn, remember, and make complex decisions. Thus, the present inventor believes that electrical stimulation of a cranial nerve can cause morphological, chemical, and neurophysiological changes to the matrix (neuronal networks, cerebrum etc). The present inventor contemplates that, in combination with the changes seen in the same matrix during normal development, reorganization of the matrix by electrical stimulation of a cranial nerve is well suited to improve functional recovery after stroke of any kind.

The methods may further comprise producing the stimulating electrical signal. The stimulating electrical signal may be produced with a stimulus generator. The stimulus generator may be implanted within the human or animal subject's body.

The stimulating electrical signal may be applied to one or more cranial nerves. When one cranial nerve is stimulated, such as the vagus nerve, this is herein termed unilateral, e.g., unilateral application of the stimulating electrical signal. The stimulating electrical signal may be applied to two cranial nerves. When two cranial nerves of the same type are stimulated, this is herein termed bilateral, e.g. bilateral application of the stimulating electrical signal. When the stimulating electrical signal is applied to two cranial nerves, the signal may be alternated between the two nerves.

The stimulating electrical signal may be applied for stimulation of the afferent fibers of the cranial nerve. The afferent fibers are those extending toward the brain. Alternately, or in combination, the stimulating electrical signal may be applied for stimulation of the efferent fibers of the cranial nerve. The efferent fibers are those extending from the brain. When the stimulating electrical signal is applied to the afferent fibers alone, this is herein termed unidirectional stimulation. Likewise, when the stimulating electrical signal is applied to the efferent fibers alone, this is herein termed unidirectional stimulation. When the stimulating electrical signal is applied to both the afferent and efferent fibers, this is herein termed bi-directional stimulation.

The stimulating electrical signal may supply a current to the cranial nerve in the range of from about 0.1 mA to about 10 mA for implantable electrodes and higher for transcutaneous stimulation. For example, the present inventor contemplates a typical current of about 1.25 mA. The stimulating electrical signal may comprise a train of pulses, each pulse having a pulse width ranging from about 50 microseconds to about 1,500 microseconds. For example, the present inventor contemplates a typical pulse width of about 250 microseconds. The stimulating electrical signal may comprise a train of pulses each pulse having a frequency ranging from about 1 Hz to about 200 Hz. For example, the present inventor contemplates a typical frequency of about 20 Hz. The stimulating electrical signal may be monophasic, biphasic, or a combination thereof.

The electrical signal may comprise a train of pulses having a train duration ranging from about 5 milliseconds to about 8 hours, and each train may have different characteristics such as frequency and pulse width etc. For example, the electrical signal may comprise a plurality of trains of pulses, each train having a train duration ranging from about 5 milliseconds to about 8 hours. The plurality of trains may have an interval between trains ranging from about 0.25 seconds to about 1 month. The plurality of trains may be a plurality of intervals, each ranging from about 0.25 seconds to about 1 month. The trains may be supplied on demand.

The frequency of a plurality of pulse trains may change between each pulse train. The frequency of the plurality of pulse trains may change for each pulse train. The output of a pulse train may change during the pulse train. The output of a plurality of pulse trains may change between each pulse train. The pulse trains may be delivered only when the device detects a stroke-related dysfunction. Alternately, the pulse trains may be delivered only during specified times of the day.

The electrical stimulation may provide stimulation to control a concomitant dysfunction. The stimulation may be applied together with detection of the concomitant dysfunction. Concomitant dysfunctions that may be detected include, but are not limited to include, post-stroke epilepsy, high blood pressure, cardiac arrhythmia, non-stroke induced swallowing dysfunction, and the like.

The method may comprise signals alternating to control a concomitant dysfunction and to promote stroke recovery. That is, signals alternately directed to control of the concomitant dysfunction and promotion of stroke recovery may be applied. One cranial nerve may be stimulated to promote stroke recovery. Another cranial nerve may be stimulated to control cardiac arrhythmia, for example.

To treat a combination of stroke and various co-morbid disorders, for instance, dysphagia, muscle weakness and prevention of post stroke depression the device can automatically alternate stimulating parameters and, for instance, use 4 hours of stimulation parameters specifically for stroke and 2 hours each of parameter settings for depression or dysphagia each in each 8 hour block.

A swipe of the magnet may activate a stimulation parameter for a co-morbid disorder. For example, a swipe of a magnet may activate the dysphagia stimulation parameter for a preset amount of time when the patient is eating or drinking. A suitable magnet is disclosed in U.S. Pat. No. 5,154,172. Suitable magnets are available commercially in a device kit available from Cyberonics, Inc. It will be understood that a swipe (also herein termed sweep) of a magnet is illustrative of delivery of stimulation on demand. Further, dysphagia stimulation is illustrative of stimulation for concomitant dysfunction. These examples are illustrative of methods for improving functional recovery after stroke in which stimulation of the concomitant dysfunction is delivered on demand by a sweep of the magnet or by other means of activation. The stimulation may last for a preset amount of time. For example, a sweep of the magnet could activate the thalamic pain stimulation parameter for a preset amount of time when the patient is experiencing increased pain. Alternatively or in combination, for example, the magnet could also be used to activate stimulation against gait instability when a patient is mobile. RF activation by the patient is another possibility when the patient is unable to use the magnet. The patient could, for instance, press a transmit button with a hand, arm, leg, or foot to activate the device. A suitable RF activation circuitry is disclosed in U.S. Pat. No. 7,110,823.

The stimulating electrical signal may supply a current to the cranial nerve in the range of from about 0.1 mA to about 10 mA for implantable electrodes and higher for transcutaneous stimulation. In the case of treating co-morbid disorders, for example, dysphagia (swallowing difficulties), stimulating frequencies of about 10 Hz, stimulating intensities of about 1 mA, pulse widths of about 200 microseconds, and an ON time of about 1 minute are expected to be most effective. Another example is suppression of epileptogenesis caused by stroke, in which an ON time of about 30 minutes and an OFF time of about 60 minutes, stimulating intensities of about 1.25 mA and pulse widths of about 250 microseconds are expected to be most effective. For recovery of motor functions caused by stroke, stimulating frequencies of about 15 Hz, ON times of about 5 minutes and OFF times of about minutes, stimulating intensities of about 1.5 mA and higher, and pulse widths of 200 microseconds are expected to be most effective. For tremor caused by stroke, ON and OFF times of about 10 minutes, stimulating frequencies of about 10 Hz, stimulating intensities of about 1.5 mA, and pulse widths of about 250 microseconds are expected to be most effective.

It will be understood that the electrical stimulation may further increase collateral blood flow to the brain. Stroke disrupts blood flow to the brain. Vagus nerve stimulation therapy geared towards restoring blood flow to a heart muscle has been described (Terry, et al. U.S. Pat. No. 6,473,644). When the electrical stimulation further increases collateral blood flow to the brain, distinct parameter sets may apply for other stimulation as described herein and for the electrical stimulation restoring blood flow. As described herein, stimulation directed at different effects may alternate to the same cranial nerve or be applied to different cranial nerves.

It will be understood that a dormant device may be prophylactically implanted in patients that are at a high risk of developing a stroke. These patents may include, but are not limited to, patients who have recently, (within the last 12 months), experienced a TIA (trans-ischemic attack), atrial fibrillation with or without a patent foramen ovale, hematological, infectious, or cancerous conditions that increases the risk for coagulation. By activating the internal generator with either an external device or a tap a pre-set combination of stimulation parameters may be activated. That stimulation continues automatically until the patient is under the care of a physician who can, if needed, change the parameters. This procedure may also be used in patients that experience a second or third stroke.

It will be understood that a device may be left dormant, after an initial acute treatment of, for example, 6 to 12 months, in the patient after a first stroke. The device may be re-activated by a tap or a sweep of the magnet if and when the patient has a subsequent stroke. Further, intermittent activation may also be used for periodic illnesses, such as more weakness in previous afflicted body parts due to an infection, fever, or the like without a new stroke, or intermittently increased pain symptoms.

The present inventors believe that vagus nerve stimulation is capable of affecting the immune system. Once infected by a disease agent, such as, for example, a virus, vagus nerve stimulation may ameliorate the symptoms and decrease the inflammatory response. Further, vagus nerve stimulation may ameliorate autoimmune disorders such as psoriasis and rheumatological disorders as well.

It will be understood that stroke treatment and recovery may involve more than modulating brain plasticity. Effective stroke treatment desirably further involves traditional rehabilitation. Acute ischemic strokes are conventionally treated by TPA or other drugs aimed to increase blood flow to the infarcted areas. This contrasts with conventional treatment of traumatic brain injury. Traumatic brain injury is more similar to a brain hemorrhage combined with a high level of edema (swelling) and increased intracranial pressure and is not treated by TPA which would worsen the situation. However, common treatment options include surgery to relieve intracranial pressure and/or to close severed cranial arteries.

Figure 1:
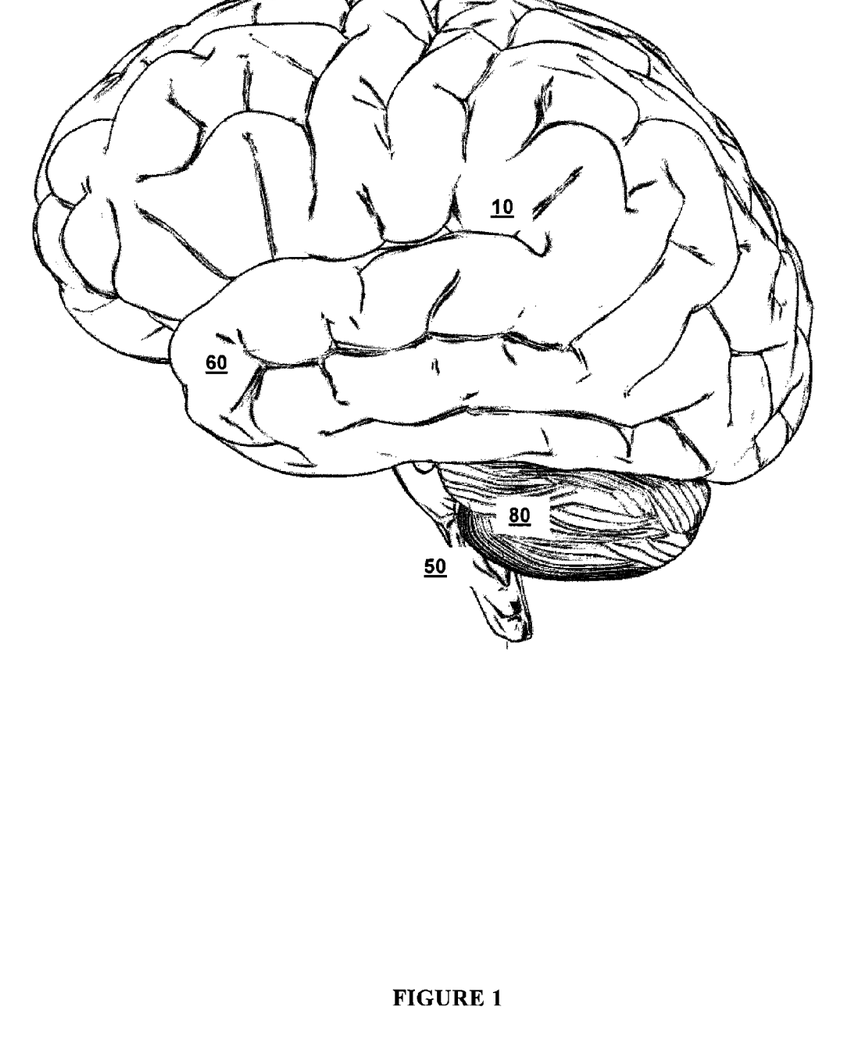
FIG. 1 is a lateral view of an exemplary human brain.
Figure 2:
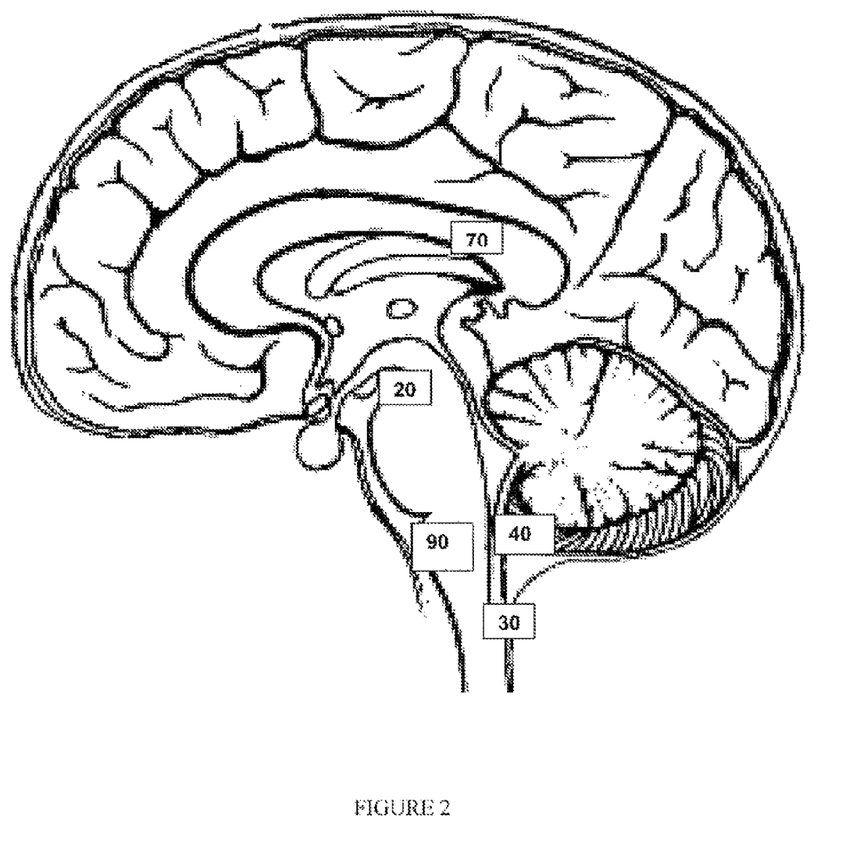
FIG. 2 is a cross-sectional view of an exemplary human brain.
Figure 3:
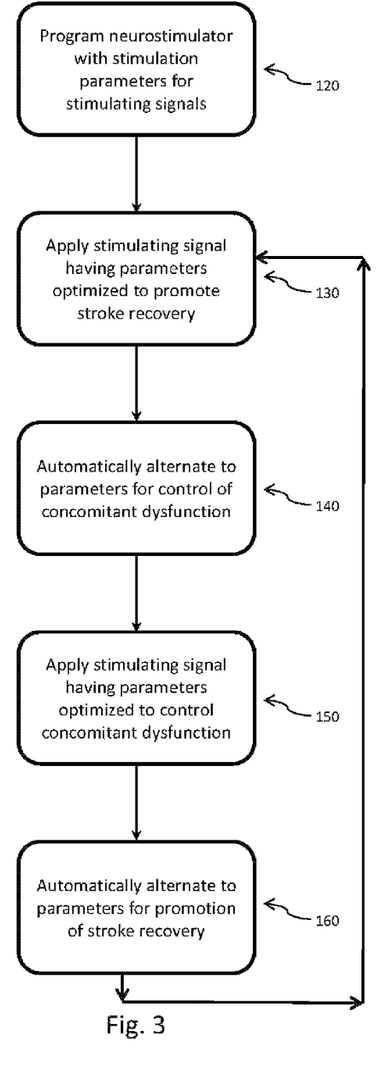
FIGS. 3 and 4 are flow diagrams of respective methods of improving functional recovery after stroke.
Figure 4:
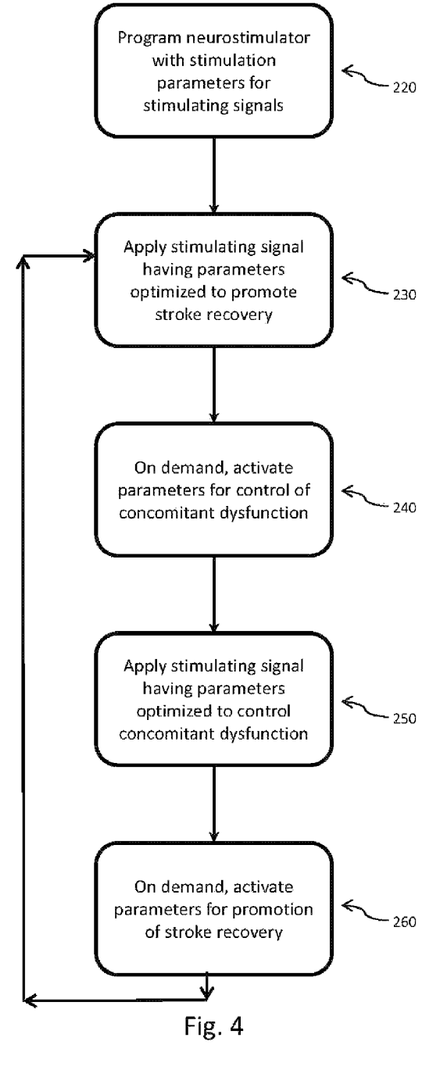

It will be understood that the stimulating signals described herein are exemplary and not limiting. Referring to FIGS. 1-2, further examples of stimulating signals and their optimization follow. Thus, referring to FIG. 3, an exemplary method of improving functional recovery from stroke may involve steps of 130 applying a first signal optimized for stroke recovery, and 150 applying a second signal optimized for control of concomitant dysfunction, and further 120 programming a nuerostimulator with stimulation parameters for the stimulating signals, and 140 and 160 automatically alternating stimulation parameters. Further, referring to FIG. 4, an exemplary method of improving functional recovery from stroke may involve 230 applying a first signal optimized for stroke recovery, and 250 applying a second signal optimized for control of concomitant dysfunction, and further 220 programming a nuerostimulator with stimulation parameters for the stimulating signals, and 240 and 260 on demand activating stimulation parameters. It is believed by the present inventor that stimulating signals directed to different forms of recovery may alter different areas of the brain. This is illustrated with respect to some of the exemplary stimulating signals that follow.

Referring to FIG. 1, hemispheric strokes, such as involving one or more lobes 10, may be stimulated for improvement of functional recovery, with the following optimized settings: A first electrical stimulus of 30 Hz, 150-350 microseconds pulse width, 0.85-1.35 mA intensity, 1 minute ON time and 4 minutes OFF time may be applied to a vagus nerve. To increase the release of norepinephrine and dopamine, a second stimulus train of 4 single pulses at 100 Hz (pseudo-one pulse-(POP) stimulation) and 2.4 seconds OFF for a total of four minutes and may be delivered during the normal OFF time of the first electrical stimulus. The second train could be delivered to the same cranial nerve or could be delivered to the opposite vagus nerve or another cranial nerve.

The inventor believes that the use of this stimuli set has the advantage of optimizing release of signal substances which influence cortical reorganization and progenitor cell proliferation and that this particular method of electrically stimulating the brain will speed up and improve functional recovery beyond what is possible with physical therapy alone, or by other currently available methods of electrical stimulation of the central nervous system.

Depending on the type of co-morbidity a different stimulus pattern may be applied according to the type of co-morbidity. This stimulus may be intermingled with the stroke settings using the same vagus nerve or applied to a second nerve. For example of intermingling, the stimulus patterns described above could be applied for four hours followed by four hours of stimulus trains described below for specific co-morbidities. The treatment may be expanded by adding a third or more treatment segment for three or more co-morbidities and the treatment times may be shortened or lengthened as appropriate. Alternatively, the co-morbid treatments may be applied to the opposite vagus or another cranial nerve.

Referring to FIG. 2, for thalamic pain secondary to hemispheric stroke, such as involving brain region 20, a stimulus consisting of approximately ⅔ of the stroke intensity (0.6-0.9 mA) at 10-20 Hz frequency, 20 seconds ON and 18 seconds OFF for 2 hours three times daily may be used.

If the patient has tremors or dysphagia secondary to the acute stroke, such as involving brain region 30, the signal will be applied to the same or a second cranial nerve and may be of low frequency (≤10 Hz), 250 millisecond pulse width, 0.75-1.25 mA intensity, and ON and OFF times at 1 minute.

For concomitant gait instability secondary to acute stroke, such as involving cerebellum 40, that does not depend on the hemiplegia per se, a signal consisting of 0.7-1.4 mA intensity, 18-28 Hz frequency, 30 seconds ON and 30 seconds OFF for 4 hours daily may be used.

Referring again to FIG. 1, for improved bladder control, such as involving brain region 50, a low frequency stimulation may be applied for long blocks of time in the acute stage. For example, 0.6 mA intensity, 10 Hz, 130-300 ms pulse width, continuous stimulation for 3 blocks of 8 hours daily may be applied.

For concomitant depression or epilepsy, secondary to hemispheric strokes, such as involving brain region 60, a modification of the settings described in PMA application # P970003 S050 and P970003 will be used (U.S. Food and Drug administration (FDA) Pre Market Approval (PMA) 97003 Supplement 050 and PMA 970003; available at https://www.accessdata.fda.gov/scripts/cdrh/cfdocs/cfPMA/PMA.cfm?ID=7759). For epilepsy, the stimulation will consist of 20 Hz, 250 milliseconds pulse width, <1.0 mA intensity, 1 minute ON and 1 minute OFF may be applied to the same or a second cranial nerve. For post stroke depression which is more common in left hemispheric strokes, the stimulus will be 20 Hz, 0.9-1.8 mA intensity, 500 millisecond pulse width, 1 minute ON and 10 minutes OFF.

Referring again to FIG. 2, for strokes involving the thalamus and other midbrain structures, such as in midbrain 70, setting may be similar to those used for hemispheric stroke. A first electrical stimulus of 18-25 Hz, 150-350 microseconds pulse width, 0.85-1.35 mA intensity, 1 minute ON time and 4 minutes OFF time will be applied to a vagus nerve. To increase the release of norepinephrine and dopamine a second stimulus consisting of 4 single pulses at 100 Hz will be applied for 1.2 seconds every 2.4 seconds during the OFF times. There are reasons to believe that pre-synaptic dopaminergic compensation develops in residual dopaminergic terminals after a moderate lesion and that an electrical stimulus that enhances this release is able to increase functional motor recovery far beyond what is accomplished today.

Patients with diencephalic strokes, such as involving brain region 100, are highly prone to post-stroke pain and depression and for this type of co-morbidities two types of secondary stimuli are contemplated. 1) A stimulus consisting of approximately ⅔ of the stroke intensity (0.6-0.9 mA) at 15-20 Hz frequency, 20 seconds ON and 18 seconds OFF for 2 hours four or more times daily will be used for pain. 2) For post-stroke depression, a stimulus consisting of 20 Hz, 0.9-1.8 mA intensity, 500 millisecond pulse width, 1 minute ON and 10 minutes OFF can be used.

As the stroke involves deeper areas of the CNS (not shown) swallowing will become more affected. For dysphagia the inventor suggests a second stimulus consisting of <10 Hz, 250 millisecond pulse width, 0.5-1.0 mA intensity, and ON and OFF times of 1 minute.

Referring again to FIG. 1, for strokes involving the cerebellum 80, an initial stimulus may include an electrical signal of 20-25 Hz, 150-350 microseconds pulse width, 0.8-1.6 mA intensity, 1.5 minute ON time and 4 minutes OFF time to a cranial (vagus) nerve.

Referring again to FIG. 2, for strokes involving the brain stem 90, the inventor believes that POP stimulation (4 single pulses at 100 Hz, 1.2 seconds ON and 2.4 seconds OFF) is most appropriate. Lesions in the brain stem area are in close proximity to structures that normally release norepinephrine and serotonin and that are known to increase release of signal substances in respond to a low number of high frequency pulses.

Co-morbidities such as dysphagia and irregular breathing are common in this type of stroke, that is strokes involving brain stem 90. For dysphagia a stimulus consisting of 5-8 Hz, 250 millisecond pulse width, 0.75-1.0 mA intensity, 1 minute ON and 2 minutes OFF times are contemplated. For irregular breathing the POP stimulus signal may be increased in strength or combined with a second signal consisting of 25-30 Hz, 130-420 milliseconds pulse width, 1.0-1.65 mA, 1 minute ON and 3 minutes OFF during the awake hours of the day. During sleep a more intense POP signal may be used.

For immune dysfunction, the following stimulation settings may be used: 15-20 Hz, 3 minute ON time and 6 minute OFF time, 0.7-0.9 mA, 250 milliseconds pulse width, with or without stimulation of a second cranial nerve by 30 Hz, 1 hour ON and 1 hour OFF, 0.75 mA, and 250 milliseconds pulse width. Other possible stimulation parameters, include but are not limited to, 4 to 8 pulses at 100 Hz every 10 seconds during the 6 minute or 1 hour OFF interval.

A magnet, such as described above, may be used to start or abolish an ongoing stimulation for all the stroke types described above. The magnet may also function as an "ambu bag" if the patient should experience a second stroke after the initial stroke has been treated and the VNS devise is in a standby mode (i.e., the patient or a care giver can start one stimulation pattern while calling for an ambulance and the patient can be stimulated from the time of the second acute stroke and does not have to wait for evaluation by a physician). The inventor believes that, even though the efficacy of VNS increases with time, for stroke it is desirable to start stimulating as soon as possible particularly in patients experiencing a second or third event since they have already experienced cell damage from the first stroke and are more sensitive to following events.

It will be understood that electrical stimulation is illustrative of stimulation. Alternative methods of stimulation include mechanical, thermal, magnetic, chemical, and optical stimulation. A neuron will propagate an electrical impulse after applying a stimulus to the neuron. U.S. Pat. No. 4,759,377 describes an apparatus and method for mechanical stimulation of nerves. Acupuncture could also be used as a method of mechanical stimulation. U.S. Pat. No. 6,364,899 describes a thermal method of nerve stimulation incorporating a heat pipe nerve cooler. U.S. Pat. No. 5,047,005 describes a method and apparatus for magnetically stimulating neurons. Magnetic stimulation has the advantage of depolarizing deep neurons. US Patent Application 20080125829 describes a chemical method of method of brain stimulation. U.S. Pat. No. 6,921,413 describes stimulation of neural tissue to include generation and propagation of an electrical impulse in one or more neurons after applying an optical stimulus. Optical stimulation may include one or more of visible light stimulation, infrared stimulation, and the like.

It will be understood that the stimulation may include one or more of direct, tran-cutaneous, and per-cutaneous stimulation.

It will be understood that the damage caused by stroke is vastly different from that caused by traumatic brain injury. In U.S. Pat. Nos. 6,104,956 and 6,339,725, Naritoku et al. suggest using vagus nerve stimulation to improve coma, epilepsy, and memory function from damage to the temporal lobes caused by traumatic brain injury. Naritoko et al suggest that the stimulating parameters set forth in their patents would improve damage to the cortical layers of the temporal lobe. The present inventor believes that by using different stimulating parameters and/or by stimulating more than one cranial nerve, it is possible to affect many and different parts of the brain simultaneously. For instance sub-cortical nuclei, white substance (myelinated pathways and inter-hemispheric connections), and wide spread grey substance (cortical regions) simultaneously. The present inventor believes that vagus nerve stimulation, or stimulation of any other cranial nerve, could modulate the function and organization of hemispheric and extra hemispheric pathways and have a diffuse effect on the brain as a whole.

Hence, the notion of superior recovery of striate and smooth muscular functions, sensory capabilities, and verbal capacity with vagus or any other cranial nerve stimulation is based on the idea that electrical stimulation of a cranial nerve is capable of affecting many unconnected parts of the brain simultaneously and that synergetic effects cause improvement, particularly functional improvement. The synergistic effects may be the major cause of the functional improvement.

Further more, the deficits caused by and the recovery from a traumatic brain injury are different from the deficits and may be more importantly, the process of recovery after stroke. Initially after a stroke, there is an immediate loss of neurons and secondarily due to die-back, a loss of myelinated axons (pathways and intra brain connections). This starts a highly coordinated temporally and spatially cascade directing the expression/suppression of genes coding for growth stimulating and growth inhibiting proteins. Intensive local rewiring takes place: stimulation of neurite outgrowth, axonal sprouting and formation of new synapses. Periinfarct neurons become hyperexcitable, and glutamate receptors are upregulated, while GABA-ergic receptors are downregulated. If initially undamaged neurons surrounding the infarcted area are kept alive they are also able to play significant roles in subsequent functional recovery. Stoke can also increase neurogenesis, neural stem cells originating in subventricular and subgranular zones begin to migrate to the injury site after stroke, where they are able to mature into newly generated neurons. These processes are closely linked to the invasion of the periinfarct area by endothelial progenitor cells and angiogenesis, which promote neuronal maturation and revascularization of the damaged area.

In the case of traumatic, penetrating or otherwise brain injury, there is typically an immediate disruption of myelinated axons (pathways) see for recent reference Topal et al Neurol Res 2008, and a secondary wide spread loss of neurons typically combined with a high level of edema (swelling) and increased intracranial pressure. TBI initiates a neuroinflammatory cascade characterized by activation of astrocytes and microglia, and increased production of immune mediators including proinflammatory cytokines and chemokines. This inflammatory response contributes both to the acute pathologic processes including cerebral edema, and longer-term neuronal death, inflammation, and glial scarring.

For example, patients with post-traumatic language processing deficits recover most language functions and some cognitive functions at a higher degree than patients suffering from language deficits from stroke. There is also a greater correlation within language and cognitive functions, as well as between language functions and other aspects of cognition in patients with post-traumatic language processing deficits than in patients with aphasia following a stroke. Clinically patients with post-traumatic language processing deficits have a different recovery pattern and a different pattern of correlation between language and cognitive functions compared to patients with aphasia following a stroke.

The patents and publications cited herein are hereby incorporated by reference herein to the extent that they do not conflict with the present description.

Although the invention has been described with reference to specific embodiments, these descriptions are not meant to be construed in a limiting sense. Various modifications of the disclosed embodiments, as well as alternative embodiments of the invention, will become apparent to persons skilled in the art upon reference to the description of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

It is therefore contemplated that the claims will cover any such modifications or embodiments that fall within the true scope of the invention.

What is claimed is:

1. A method for improving functional recovery after stroke in a human or animal in need thereof, said method comprising:
    (a) applying to a first cranial nerve a first stimulating signal optimized so as to promote stroke recovery, wherein the stroke recovery is evidenced by improvement to one or more of factors diminished by stroke, wherein the factors are selected from the group consisting of motor strength, fine motor movements, sensory, balance, swallowing, thalamic pain, language, memory, and continence; and
    (b) applying to one or more of the first cranial nerve and a second cranial nerve a second stimulating signal optimized so as to control a concomitant dysfunction, wherein the first and second cranial nerves are opposite vagus nerves and wherein the concomitant dysfunction is one or more of dysfunctions selected from the group consisting of post-stroke mood disorder, post-stroke epilepsy, coma, high blood pressure, and cardiac arrhythmia.

2. The method according to claim 1, wherein the first stimulating signal and the second stimulating signal automatically alternate with each other.

3. The method according to claim 1, wherein one or both of the first stimulating signal and the second stimulating signal is applied on demand.

4. The method according to claim 1, wherein the concomitant dysfunction comprises post-stroke depression.

5. The method according to claim 1, wherein the concomitant dysfunction comprises post-stroke epilepsy.

6. The method according to claim 1, wherein the concomitant dysfunction comprises coma.

7. The method according to claim 1, wherein the concomitant dysfunction comprises high blood pressure.

8. The method according to claim 1, wherein the concomitant dysfunction comprises cardiac arrhythmia.

9. The method according to claim 1, wherein the method further comprises:
    (c) detecting the level of the concomitant dysfunction; and
    (d) automatically initiating the second stimulating signal.

10. The method according to claim 1, wherein the first cranial nerve is a vagus nerve; and wherein the first stimulating signal is applied to the vagus nerve and the second stimulating signal is applied to the vagus nerve.

11. The method according to claim 1, wherein the factor is selected from the group consisting of motor strength, fine motor movements, and balance; and wherein the concomitant dysfunction is post-stroke mood disorder.

12. The method according to claim 1, wherein the first and second stimulating signals are selected so as to affect different parts of the brain.

13. The method according to claim 12, wherein the first and second stimulating signals synergistically cause the improving functional recovery.

14. The method according to claim 1, wherein the stroke recovery comprises neurophysiological, morphological, chemical, or neuronal connective alteration in the brain of the human or animal, wherein the alternation changes a neural function in the brain so as to change functional stroke recovery in the human or animal.

15. The method according to claim 1, wherein the concomitant dysfunction comprises a disability introduced by stroke.

16. The method according to claim 1, wherein one or more of the first and second stimulation signals are generated by an implanted stimulus generator.

17. The method according to claim 16, wherein the method further comprises, before steps (a) and (b):
   (c) applying to one or more of the first and second cranials nerves a third stimulating signal optimized so as to promote stroke recovery, wherein the stimulating signal is applied externally early after the stroke during stabilization of the human or animal.

18. A method for improving functional recovery after stroke in a human or animal in need thereof, said method comprising:
   (a) applying to a first vagus nerve a first stimulating signal optimized so as to promote stroke recovery comprising neurophysiological, morphological, chemical, or neuronal connective alteration in the brain of the human or animal, wherein the alternation changes a neural function in the brain so as to change functional stroke recovery in the human or animal, wherein the stroke recovery is evidenced by improvement to one or more of factors diminished by stroke, wherein the factors are selected from the group consisting of motor strength, fine motor movements, and balance; and
   (b) applying to one or more of the first vagus nerve and a second vagus nerve a second stimulating signal optimized so as to control a concomitant dysfunction, wherein the first vagus nerve and the second vagus nerve are opposite vagus nerves, wherein the concomitant dysfunction comprises a disability introduced by stroke, wherein the concomitant dysfunction is post-stroke mood disorder;
   wherein the first and second stimulating signals are selected so as to affect different parts of the brain; and
   wherein the first and second stimulating signals synergistically cause the improving functional recovery;
   wherein one or more of the first and second stimulation signals are generated by an implanted stimulus generator.

19. The method according to claim 18, wherein the second stimulating signal is applied to the second vagus nerve.

20. The method according to claim 19, wherein the second stimulating signal is applied to the first vagus nerve.

21. The method according to claim 18,
   wherein the method further comprises, before steps (a) and (b):
   (c) applying to one or more of the first and second vagus nerves a third stimulating signal optimized so as to promote stroke recovery, wherein the stimulating signal is applied externally early after the stroke during stabilization of the human or animal.

* * * * *